(12) United States Patent
Liu et al.

(10) Patent No.: US 9,994,496 B2
(45) Date of Patent: Jun. 12, 2018

(54) METHOD FOR PREPARING P-XYLENE AND PROPYLENE FROM METHANOL AND/OR DIMETHYL ETHER

(71) Applicant: DALIAN INSTITUTE OF CHEMICAL PHYSICS, CHINESE ACADEMY OF SCIENCES, Dalian (CN)

(72) Inventors: Zhongmin Liu, Dalian (CN); Lei Xu, Dalian (CN)

(73) Assignee: DALIAN INSTITUTE OF CHEMICAL PHYSICS, CHINESE ACADEMY OF SCIENCES, Dalian (CN)

( * ) Notice: Subject to any disclaimer, the term of this patent is extended or adjusted under 35 U.S.C. 154(b) by 22 days.

(21) Appl. No.: 15/315,768

(22) PCT Filed: Jun. 4, 2014

(86) PCT No.: PCT/CN2014/079141
§ 371 (c)(1),
(2) Date: Dec. 2, 2016

(87) PCT Pub. No.: WO2015/184598
PCT Pub. Date: Dec. 10, 2015

(65) Prior Publication Data
US 2017/0166494 A1 Jun. 15, 2017

(51) Int. Cl.
*C07C 1/20* (2006.01)
(52) U.S. Cl.
CPC ............ *C07C 1/20* (2013.01); *C07C 2529/40* (2013.01); *C07C 2529/44* (2013.01); *Y02P 20/52* (2015.11); *Y02P 20/584* (2015.11)

(58) Field of Classification Search
CPC ... C07C 1/20; C07C 2529/40; C07C 2529/44; Y02P 20/52; Y02P 20/584
See application file for complete search history.

(56) References Cited

U.S. PATENT DOCUMENTS 3,911,041 A 10/1975 Kadeing et al.
4,035,430 A 7/1977 Dwyer et al.
(Continued)

FOREIGN PATENT DOCUMENTS

CN 1880288 A 12/2006
CN 101244969 A 8/2008
(Continued)

OTHER PUBLICATIONS

Office Action issued by Japan Patent Office for related Japanese Patent Application No. JP2016-571198 dated Jan. 30, 2018.
(Continued)

*Primary Examiner* — Brian A McCaig
*Assistant Examiner* — Jason Y Chong
(74) *Attorney, Agent, or Firm* — Enshan Hong; VLP Law Group LLP (57) ABSTRACT

This invention relates to a method for preparing p-xylene and propylene from methanol and/or dimethyl ether. This method comprises coupling two reaction processes, an aromatization reaction of methanol and/or dimethyl ether and an alkylation reaction of ethylene with methanol and/or dimethyl ether. The method of this invention produces p-xylene and propylene with a high selectivity by returning an ethylene-enriched component in reaction byproducts from preparation of p-xylene from methanol and/or dimethyl ether to the reaction system for performing alkylation reaction with methanol and/or dimethyl ether in the presence of catalysts.

8 Claims, 4 Drawing Sheets (56) References Cited

U.S. PATENT DOCUMENTS

| | | | |
|---|---|---|---|
| 4,049,573 A | 9/1977 | Kadeing et al. | |
| 4,100,219 A | 7/1978 | Rodewald et al. | |
| 4,542,252 A | 9/1985 | Graziani et al. | |
| 4,615,995 A | 10/1986 | Mao | |
| 5,367,100 A | 11/1994 | Wang et al. | |
| 2008/0242910 A1* | 10/2008 | Kalnes | C07C 1/20 585/640 |
| 2009/0124841 A1* | 5/2009 | Rothaemel | B01D 3/143 585/639 |
| 2010/0217054 A1* | 8/2010 | Ito | B01J 29/04 585/300 |

FOREIGN PATENT DOCUMENTS

| | | |
|---|---|---|
| CN | 101270016 A | 9/2008 |
| CN | 101602643 A | 12/2009 |
| CN | 101607858 A | 12/2009 |
| CN | 101780417 A | 7/2010 |
| CN | 101880212 A | 11/2010 |
| CN | 102190546 A | 9/2011 |
| CN | 101767038 B | 4/2012 |
| CN | 102464549 A | 5/2012 |
| CN | 102464550 A | 5/2012 |
| CN | 103387476 A | 11/2013 |
| CN | 103508832 A | 1/2014 |
| JP | 60126233 A | 7/1985 |
| JP | 6197231 A | 5/1986 |
| JP | 6270324 A | 3/1987 |

OTHER PUBLICATIONS

Office Action issued by Korean Patent Office for related Korean Patent Application No. KR10-2017-7000072 dated Feb. 13, 2018.

\* cited by examiner

METHOD FOR PREPARING P-XYLENE AND PROPYLENE FROM METHANOL AND/OR DIMETHYL ETHER

RELATED APPLICATIONS

This is a U.S. national stage of international application No. PCT/CN2014/079141 filed on Dec. 4, 2014.

TECHNICAL FIELD

This invention relates to a method for preparing p-xylene and propylene from methanol and/or dimethyl ether, and pertains to the fields of chemistry and chemical industry.

BACKGROUND ART

P-xylene (PX) and propylene are both important and valuable raw materials essential for chemical industry. At present, p-xylene is mainly obtained by an aromatic hydrocarbon combination apparatus. A reformate containing aromatic hydrocarbons is prepared by continuous reforming of naphtha, and a PX product is then maximally obtained via units of aromatic extraction, aromatic fractional distillation, disproportionation and transalkylation, xylene isomerization, and adsorptive separation, etc. Since the content of p-xylene among three isomers is thermodynamically controlled, and p-xylene comprises only about 23% in $C_8$ mixed aromatic hydrocarbons, the amount of recycling process is large, equipment is bulky, and the operational cost is high during the whole PX production process. Particularly, the differences between boiling points of three isomers of xylene are very small, high-purity p-xylene cannot be obtained with typical distillation techniques, and an expensive process for adsorptive separation has to be used. Propylene is mainly derived from byproducts in petroleum refineries and also from the production of ethylene by steam cracking of naphtha, or is produced by using propane as a raw material, which is prepared by processing of natural gas. p-Xylene is mainly used in the production of polyesters, and propylene is primarily used in the preparation of polypropylene and acrylonitrile as well as 1,3-propylene glycol required in the production of polyesters. The rapid development of the global economy increasingly demands for p-xylene and propylene as essential chemical feedstocks.

The preparation of aromatic hydrocarbons from methanol is a new route in non-petroleum schemes for preparing aromatic hydrocarbons. Chinese Patent CN 101244969 discloses a fluidized bed apparatus for aromatization of $C_1$-$C_2$ hydrocarbons or methanol and catalyst regeneration therein. With this apparatus and catalyst, the coking state of a catalyst in an aromatization reactor may be adjusted at any time so as to achieve the object of continuous and effective conversion of $C_1$-$C_2$ hydrocarbons or methanol, and highly-selective generation of aromatic hydrocarbons. Chinese Patent CN 1880288 describes a process for preparing aromatic hydrocarbons via methanol conversion. On a modified ZSM-5 molecular sieve catalyst, methanol is catalytically converted to products in which aromatic hydrocarbons predominate, of which the advantages are high selectivity for total aromatic hydrocarbons and flexible in process operation. U.S. Pat. No. 4,615,995 discloses a Zn- and Mn-loaded ZSM-5 molecular sieve catalyst for preparing olefins and aromatic hydrocarbons via methanol conversion. The ratio of light olefins/aromatic hydrocarbons in a product may be changed by adjusting the contents of Zn and Mn in the catalyst.

The preparation of olefins from methanol and the preparation of propylene from methanol are new routes in non-petroleum schemes for preparing ethylene and propylene. In 1976, Mobil Oil Corporation carried out a reaction in which methanol was converted to hydrocarbons on a ZSM-5 molecular sieve catalyst. U.S. Pat. No. 4,035,430 discloses a process for converting methanol to gasoline on a ZSM-5 molecular sieve catalyst; U.S. Pat. No. 4,542,252 discloses a technique for preparing light olefins from methanol on a ZSM-5 molecular sieve catalyst; U.S. Pat. No. 3,911,041, U.S. Pat. No. 4,049,573, U.S. Pat. No. 4,100,219, JP 60-126233, JP 61-97231, and JP 62-70324 disclose reactions for preparing light olefins from methanol by using ZSM-5 molecular sieve catalysts modified with phosphorus, magnesium, silicon, or alkali metal elements; U.S. Pat. No. 5,367,100 discloses a reaction for preparing light olefins from methanol and/or dimethyl ether using a ZSM-5 molecular sieve catalyst modified with phosphorus and lanthanum by Dalian Institute of Chemical Physics, wherein the overall selectivity of ethylene and propylene is only about 65 wt %, and the overall selectivity of ethylene, propylene, and butene is greater than 85 wt %.

CN 101767038 B and CN 101780417 B each discloses a catalyst and a method for preparing p-xylene and co-producing light olefins from methanol. It is indicated that the object of directly preparing three major essential chemicals, ethylene, propylene, and p-xylene, from methanol in one reaction process is achieved on catalysts modified with metals and silane. In hydrocarbon products obtained from the reaction, the selectivity of p-xylene in aromatic hydrocarbons is greater than 80 wt % or more, and the selectivity of ethylene and propylene in $C_1$-$C_5$ light hydrocarbons is greater than 80 wt % or more. However, the disadvantages of this method are that a cryogenic separation technique has to be used if a highly-pure ethylene product is to be obtained, and that the investment and energy consumption are both high, which directly affects the economy of this process.

Moreover, CN 101780417 B relates to a method for preparing p-xylene and light olefins (namely ethylene and propylene) via methanol conversion, which does not involve the processes of recycling ethylene-enriched $C_2^-$ components and further performing alkylation with methanol to increase the production of propylene in order to further increase the production of propylene and circumvent the difficulty of ethylene separation. CN102464550 A discloses a method for co-production of light olefins and p-xylene, comprising preparing olefins by passing C4 and C5 hydrocarbons into a first reaction zone, which is a process of preparing olefins by cracking of $C_4$ or liquefied gas, wherein the process for preparing propylene by the alkylation of ethylene and methanol/dimethyl ether is not involved either.

SUMMARY OF THE INVENTION

An object of this invention is to provide a method for preparing p-xylene and propylene from methanol and/or dimethyl ether.

To this end, this invention provides a method for preparing p-xylene and propylene from methanol and/or dimethyl ether, comprising the steps of:

a) bringing a raw material containing methanol and/or dimethyl ether into contact with a catalyst in a reaction system for reaction; returning an ethylene-enriched $C_2^-$ component discharged from the reaction system to the reaction system, and continuing the reaction with the raw material on the catalyst to produce propylene;

b) separating a $C_6^+$ component discharged from the reaction system to obtain a product p-xylene; and c) separating a $C_3$ component discharged from the reaction system to obtain a product propylene.

In one preferred embodiment, the reaction system comprises a first reaction zone and a second reaction zone, and the method comprises the steps of:

a) passing a raw material containing methanol and/or dimethyl ether through the first reaction zone to be in contact with a catalyst I for aromatization reaction, and then into the second reaction zone to be in contact with a catalyst II for alkylation reaction; returning an ethylene-enriched $C_2^-$ component discharged from the second reaction zone to the second reaction zone, and performing alkylation reaction with methanol and/or dimethyl ether within the second reaction zone on the catalyst II to produce propylene;

b) further separating a $C_6^+$ component discharged from the second reaction zone to obtain a product p-xylene; and c) further separating a $C_3$ component discharged from the second reaction zone to obtain propylene.

In one preferred embodiment, the reaction system comprises a first reaction zone and a second reaction zone, and the method comprises the steps of:

a) passing a raw material containing methanol and/or dimethyl ether through the first reaction zone to be in contact with a catalyst I for aromatization reaction to obtain a resultant A, separating the resultant A through a separation system, returning an ethylene-enriched $C_2^-$ component to the second reaction zone, and performing alkylation reaction with methanol and/or dimethyl ether passed into the second reaction zone on a catalyst II to obtain a resultant B; sequentially returning an ethylene-enriched $C_2^-$ component in the resultant A and the resultant B to the second reaction zone, and performing alkylation reaction with methanol and/or dimethyl ether within the second reaction zone in contact with the catalyst II to produce propylene;

b) further separating a $C_6^+$ component in the resultant A and the resultant B to obtain a product p-xylene; and c) further separating a $C_3$ component in the resultant A and the resultant B to obtain a product propylene.

In one preferred embodiment, the catalyst, the catalyst I, and the catalyst II contain the same or different modified zeolite molecular sieve catalyst(s).

In one preferred embodiment, the modified zeolite molecular sieve catalyst is obtained from ZSM-5 and/or ZSM-11 zeolite molecular sieves by modification with a precious metal and a rare earth metal and modification of a siloxanyl compound.

In one preferred embodiment, in the modified zeolite molecular sieve catalyst, the content of the precious metal is 0.1-10 wt % based on the total weight of the catalyst.

In one preferred embodiment, the content of the rare earth metal is 0.1-5 wt % based on the total weight of the catalyst.

In one preferred embodiment, the amount of Si loaded by siloxanyl compound modification is 1-10 wt % based on the total weight of the modified zeolite molecular sieve catalyst.

In one preferred embodiment, the precious metal is silver; and the rare earth metal is lanthanum.

In one preferred embodiment, the siloxanyl compound used in the siloxanyl compound modification has a structural formula as shown below:

wherein $R_1$, $R_2$, $R_3$, and $R_4$ are each independently a $C_{1-10}$ alkyl group.

In one preferred embodiment, the siloxanyl compound is tetraethyl orthosilicate.

In one preferred embodiment, the reaction zone comprises a reactor or a plurality of reactors connected in series and/or in parallel; and preferably, the reactor is one or more selected from a fixed bed reactor, a fluidized bed reactor, and a moving bed reactor.

In one preferred embodiment, the first reaction zone and the second reaction zone are in the same reactor; and preferably, the reactor is one or more selected from a fixed bed reactor, a fluidized bed reactor, and a moving bed reactor.

In one preferred embodiment, the first reaction zone comprises a reactor or a plurality of reactors connected in series and/or in parallel; the second reaction zone comprises a reactor or a plurality of reactors connected in series and/or in parallel; and the first reaction zone and the second reaction zone are connected in series or in parallel. And preferably, the reactor is one or more optionally selected from a fixed bed reactor, a fluidized bed reactor, and a moving bed reactor.

The advantageous effects of this invention include, but are not limited to, the following aspects: this invention provides a new method for preparing p-xylene and propylene from methanol and/or dimethyl ether, wherein an ethylene-enriched $C_2^-$ component in reaction products is recycled and subjected to an alkylation reaction with methanol and/or dimethyl ether to further produce propylene, and p-xylene and propylene are finally obtained with a high selectivity. On one hand, high cost for separation of the ethylene product is avoided, and on the other hand, the production of propylene product with larger market demand may be further increased, such that the economy of this technique may be effectively improved.

DESCRIPTION OF EMBODIMENTS

In the method of this invention, two reaction processes, an aromatization reaction of methanol and/or dimethyl ether and an alkylation reaction of ethylene with methanol and/or dimethyl ether, are combined, consequently, p-xylene and propylene are prepared with a high selectivity. Specifically, methanol and/or dimethyl ether as raw materials are brought into contact with a catalyst (the catalyst is present in a reactor) in a reaction system for aromatization reaction, and resultant products are passed into a separation system (for example, a fractionating tower, etc.) for separation; after separation by the separation system, a $C_6^+$ component (aromatic hydrocarbons having carbon number equal to or greater than 6), a $C_4$-$C_5$ component (hydrocarbons having carbon number of 4 and 5), a $C_3$ component (propylene and propane having a carbon number equal to 3), and an ethylene-enriched $C_2^-$ component (hydrocarbons having carbon number less than or equal to 2, CO, $CO_2$, and $H_2$), and water ($H_2O$) are obtained, wherein, the ethylene-enriched $C_2^-$ component is returned to the reaction system, the $C_6^+$ component is subjected to further separation (for example, a rectification column, a crystallization separation system, etc.) to obtain p-xylene, the $C_3$ component is subjected to further separation (for example, a rectification column, etc.) to obtain propylene, and a small amount of the $C_4$-$C_5$ component and $H_2O$ are collected and used for other purposes. Here, the reaction system may be a separate reaction zone, or may be a combination of two or more reaction zones. A plurality of reaction zones may be in the same reactor, or may be in a plurality of reactors connected in series or in parallel. Preferably, the reactor is any one or more of a fixed bed, a fluidized bed, or a moving bed.

Figure 1:
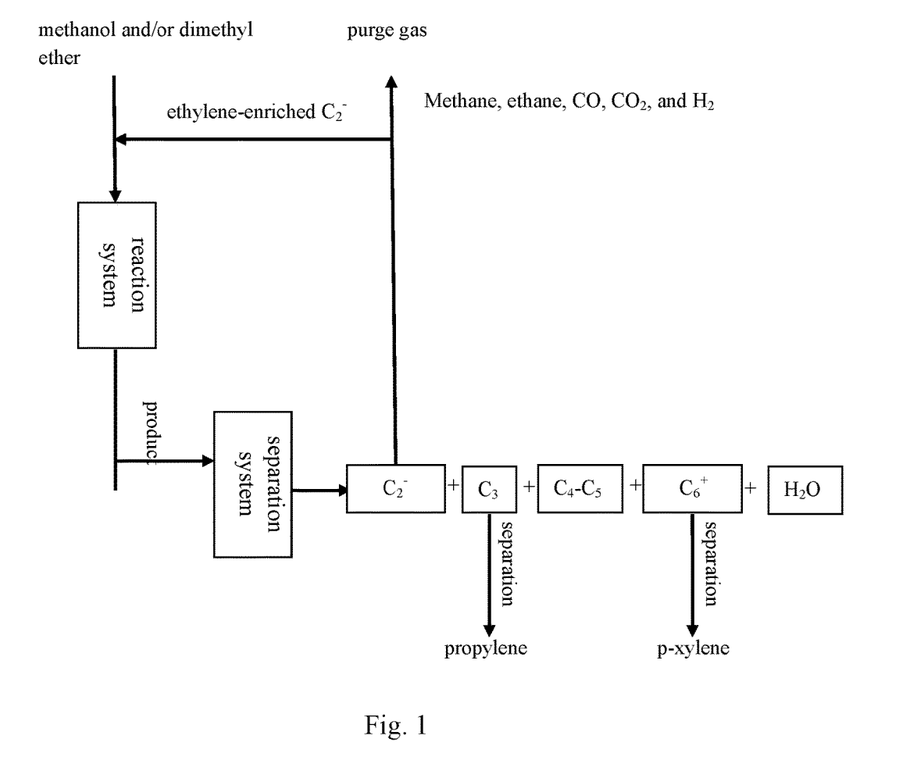
FIG. 1 is a flow chart of a method of an embodiment according to this invention.

In one preferred embodiment, a reaction process flow of a method according to this invention is as shown in FIG. 1. In FIG. 1, the reaction system is composed of one reactor having one reaction zone, wherein methanol and/or dimethyl ether as raw materials are brought into contact with a catalyst in the reaction zone of the reaction system for reaction, after separation of resultant products by a separation system, a $C_6^+$ component, a $C_4$-$C_5$ component, a $C_3$ component, a $C_2^-$ component (including an ethylene-enriched $C_2^-$ component and purge gas), and $H_2O$ are obtained, and wherein, the ethylene-enriched $C_2^-$ component is returned to the reaction system, the $C_6^+$ component is subjected to further separation to obtain p-xylene, and the $C_3$ component is subjected to further separation to obtain propylene.

Figure 2:
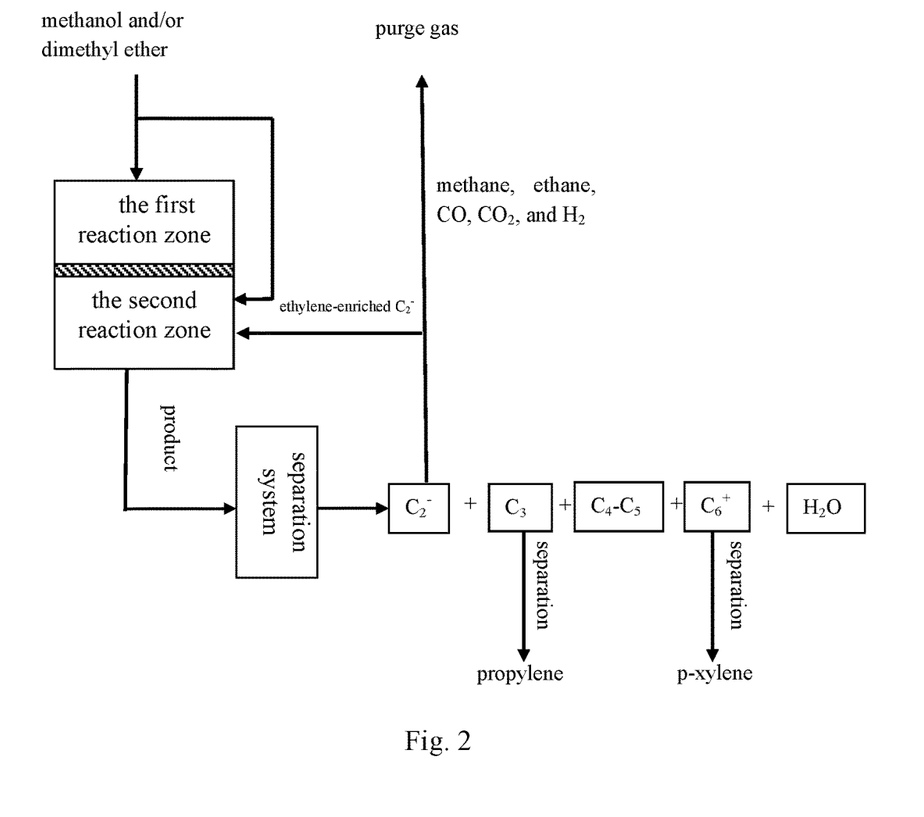
FIG. 2 is a flow chart of a method of another embodiment according to this invention.

In one preferred embodiment, a reaction process flow of a method according to this invention is as shown in FIG. 2. In FIG. 2, the reaction system is composed of one reactor having two reaction zones, wherein the main reaction in the first reaction zone is aromatization reaction of methanol and/or dimethyl ether, and the main reaction in the second reaction zone is alkylation reaction between ethylene (a byproduct of the first reaction zone) and methanol and/or dimethyl ether. Methanol and/or dimethyl ether as raw materials are passed through the first reaction zone to be in contact with a catalyst I therein for reaction, and then passed through the second reaction zone to be in contact with a catalyst II therein for reaction, and resultant products are passed into a separation system for separation; after separation by a separation system, a $C_6^+$ component, a $C_4$-$C_5$ component, a $C_3$ component, a $C_2^-$ component (including an ethylene-enriched $C_2^-$ component and purge gas), and $H_2O$ are obtained, wherein the ethylene-enriched $C_2^-$ component is returned to the second reaction zone and subjected to alkylation reaction with methanol and/or dimethyl ether that are passed into the second reaction zone in contact with the catalyst II; the $C_6^+$ component is subjected to further separation to obtain p-xylene, and the $C_3$ component is subjected to further separation to obtain propylene.

Figure 3:
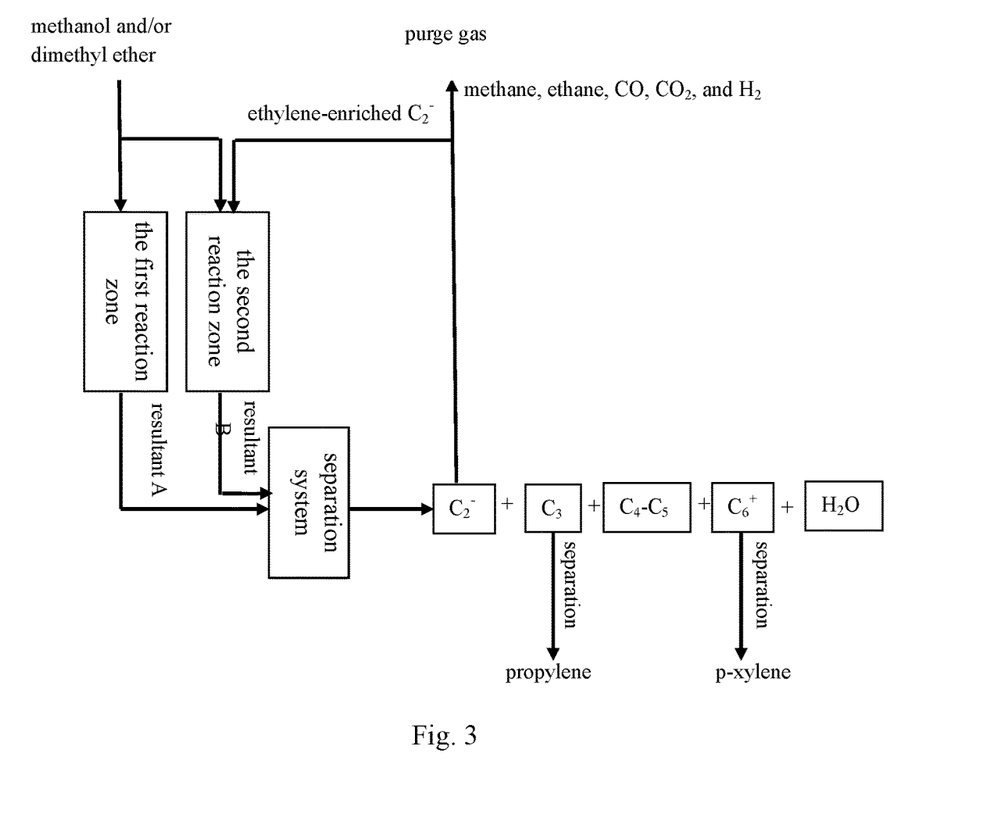
FIG. 3 is a flow chart of a method of another embodiment according to this invention.

In one preferred embodiment, a reaction process flow of a method according to this invention is as shown in FIG. 3. In FIG. 3, the reaction system are composed of two reaction zones in two parallel reactors respectively, wherein the main reaction in the first reaction zone is aromatization reaction of methanol and/or dimethyl ether, and the main reaction in the second reaction zone is alkylation reaction between ethylene (a byproduct of the first reaction zone) and methanol and/or dimethyl ether. Methanol and/or dimethyl ether are brought into contact with a catalyst I in a reaction zone for aromatization to generate a resultant A, and the resultant A is passed into a separation system for separation; an ethylene-enriched $C_2^-$ component obtained after separation is returned to the second reaction zone and subjected to alkylation reaction with methanol and/or dimethyl ether that are passed into the second reaction zone on a catalyst II to generate a resultant B, and the resultant B is passed into a separation system for separation; after separation by the separation system, the ethylene-enriched $C_2^-$ component therein is returned to the second reaction zone, a $C_6^+$ component therein, which is obtained after the resultant A and the resultant B are separated by a separation system, is subjected to further separation to obtain p-xylene, and the $C_3$ component is subjected to further separation to obtain propylene.

Figure 4:
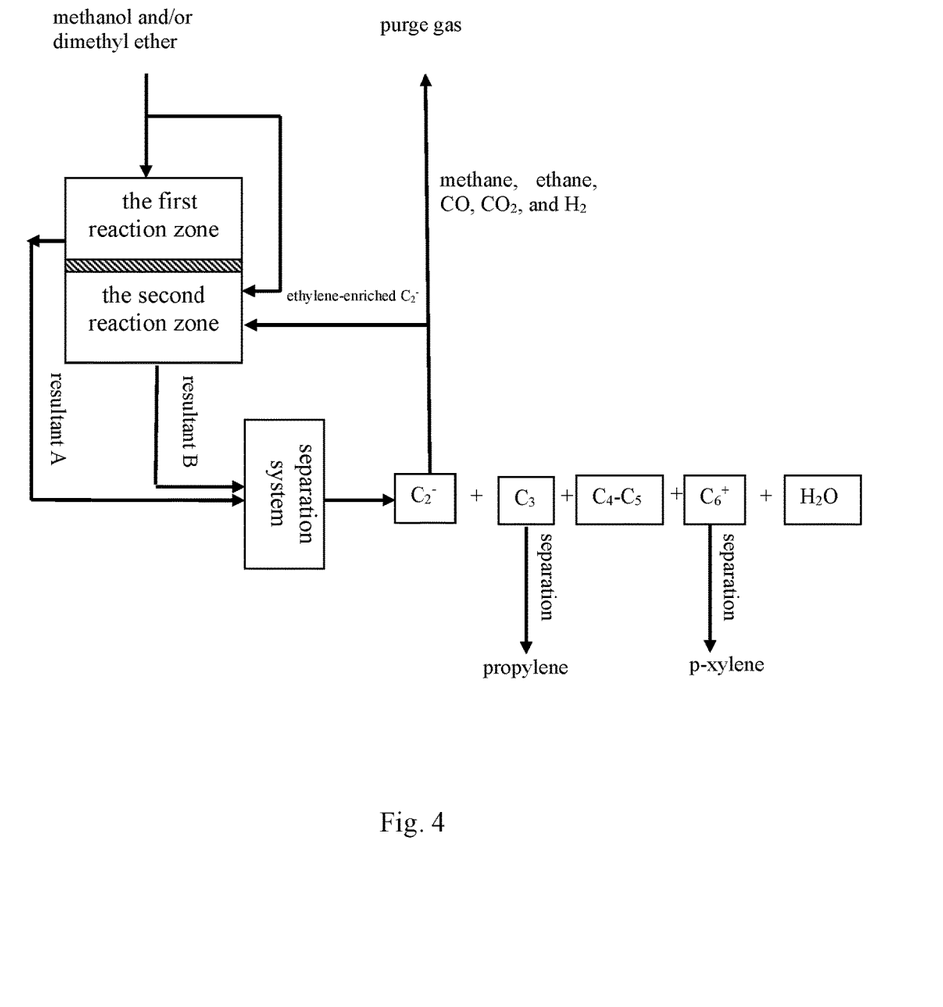
FIG. 4 is a flow chart of a method of another embodiment according to this invention.

In one preferred embodiment, a reaction process flow of a method according to this invention is as shown in FIG. 4. In FIG. 4, the reaction process is the same as the above process described for FIG. 3, except that the reaction system is composed of two reaction zones in the same reactor, and verbose words are omitted herein. This reaction system may be achieved by multi-sectional feeding.

In this invention, the catalysts used are modified ZSM-5 and/or ZSM-11 zeolite molecular sieve catalysts, which are obtained from ZSM-5 and/or ZSM-11 zeolite molecular sieves by a combined modification with a precious metal and a rare earth metal as well as a surface modification with a siloxanyl compound. When there are two reaction zones, the catalyst I and the catalyst II present therein respectively may be the same or different catalyst(s). For example, in one preferred embodiment, the catalyst I and the catalyst II are the same kind of catalysts or the same catalyst. More preferably, in this invention, after the catalyst, the catalyst I, or the catalyst II used is subjected to surface modification with a siloxanyl compound, the loading amount of Si is 1-10 wt % based on the total weight of this catalyst.

In one preferred embodiment, the preparation process of the catalyst used in this invention is as follows.

(1) ZSM-5 and/or ZSM-11 zeolite molecular sieve raw powders are prepared into acidic zeolite molecular sieves by $NH_4^+$ ion exchange and calcining.

(2) the above acidic zeolite molecular sieves are impregnated in a soluble salt solution of a precious metal and a soluble salt solution of a rare earth metal to obtain metal modified zeolite molecular sieves.

(3) the above metal modified zeolite molecular sieves are subjected to a surface modification by using a siloxanyl agent to further adjust the outer surface acidity and the pore structure of the molecular sieves so as to obtain modified zeolite molecular sieve catalysts.

Preferably, in this invention, after the catalyst, the catalyst I, or the catalyst II used is subjected to a combined modification of a precious metal and a rare earth metal, the loading amount of the precious metal is 0.1-10 wt % based on the total weight of this catalyst; and the loading amount of the rare earth metal is 0.1-5 wt % based on the total weight of this catalyst.

Preferably, the precious metal used in this invention is silver; the rare earth metal is lanthanum, which is used in the form of its soluble salt.

Preferably, the siloxanyl compound used in this invention is has a formula as shown below:

wherein $R_1$, $R_2$, $R_3$, $R_4$ are each independently a $C_{1-10}$ alkyl group, such as a methyl group, an ethyl group, a propyl group, a butyl group, a pentyl group, a hexyl group, a heptyl group, and a octyl group, as well as isomeric forms thereof.

Preferably, the siloxanyl compound used is tetraethyl orthosilicate.

Preferably, in either the first reaction zone or the second reaction zone in this invention, a fixed bed reaction process may be used, meanwhile a fluidized bed or moving bed reaction process in conjunction with a regenerator may be used. The first reaction zone and the second reaction zone may be respectively in one reactor or a plurality of reactors connected in series or in parallel, being the same or different, and are achieved by multi-sectional feeding.

In the method of this invention, the temperature of aromatization reaction of methanol and/or dimethyl ether and the temperature of alkylation reaction of ethylene and methanol and/or dimethyl ether are in the range 300-600° C. The preferred reaction temperature of aromatization reaction of methanol and/or dimethyl ether is 450-520° C., and the preferred reaction temperature of alkylation reaction of ethylene and methanol and/or dimethyl ether is 350-500° C.

In the method of this invention, the mass hourly space velocity of feeding for aromatization reaction of methanol and/or dimethyl ether is 0.1-10 $h^{-1}$, and preferably 1-5 $h^{-1}$, in terms of methanol and/or dimethyl ether. Here, the molar ratio of ethylene to methanol and/or dimethyl ether is arbitrarily selected in the range 0.1-10, and typically 0.5-5 is preferable.

In this invention, the $C_2^-$ component refers to a component of which the molecular formula has a carbon atom number less than or equal to 2, and includes ethylene, ethane, methane, CO, $CO_2$, together with $H_2$, etc. That is, the $C_2^-$ component comprises an ethylene-enriched $C_2^-$ component and purge gas. The purge gas is mainly ethane, methane, CO, $CO_2$, together with $H_2$, etc.

In this invention, the $C_3$ component refers to a compound of which the molecular formula has a carbon atom number equal to 3, and includes propylene, propane, etc.

In this invention, the $C_4$-$C_5$ component refers to a component of which the molecular formula has a carbon atom number equal to 4 and 5, and includes isobutane, isobutene, butane, 1-butene, 2-butene, isopentane, neopentane, n-pentane, 1-pentene, 2-pentene, etc.

In this invention, the $C_6^+$ component refers to a component of which the molecular formula has a carbon atom number greater than or equal to 6, and includes p-xylene and other aromatic hydrocarbons and derivatives thereof, etc.

This invention will be described in detail below by means of examples, but this invention is not limited to these examples.

The composition of products is analyzed online by a gas chromatograph, and the analysis conditions are:
Model: Varian CP3800
Column: CP Wax 52 CB capillary chromatographic column
Carrier gas: helium gas, 5 ml/min
Temperature of column box: 60-220° C., programmed temperature increasing at 15° C./min
Temperature of feed port: 260° C.
Detector: hydrogen flame ionization detector (FID)
Temperature of detector: 300° C.

Example 1

Preparation of Catalyst: HZSM-5 Molecular Sieve Catalyst and HZSM-11 Molecular Sieve Catalyst Modified with Silver, Lanthanum, and Silane 1) 500 g of ZSM-5 zeolite molecular sieve raw powder (Catalyst Plant of Fushun Petrochemical Company) ($SiO_2$/$Al_2O_3$=68) and 500 g of ZSM-11 zeolite molecular sieve raw powder (Catalyst Plant of Nankai University) ($SiO_2$/$Al_2O_3$=50) were calcined respectively at 550° C. to remove template agents, exchanged with 0.5 molar equivalents of an ammonium nitrate solution in a water bath at 80° C. for 4 times, dried at 120° C. in the air after exchange, and calcined at 550° C. for 3 hours so as to obtain a HZSM-5 zeolite molecular sieve and a HZSM-11 zeolite molecular sieve respectively.

2) 100 g of each of HZSM-5 and HZSM-11 zeolite molecular sieves prepared in step 1) was subjected to tablet compression molding, 40-60 mesh samples were obtained by cracking and sieving, which were impregnated with a silver nitrate ($AgNO_3$) solution having a mass concentration of 6% at ambient temperature for 4 hours, and Ag-HZSM-5 and Ag-HZSM-11 zeolite molecular sieves modified with silver were obtained by drying at 120° C. and calcining in the air at 550° C. for 6 hours after decanting the upper liquid layer.

3) Ag-HZSM-5 and Ag-HZSM-11 zeolite molecular sieves obtained in step 2) were each impregnated with a 5 wt % lanthanum nitrate solution ($La(NO_3)_3 \cdot 6H_2O$) at ambient temperature for 4 hours, and Ag—La-HZSM-5 and Ag—La-HZSM-11 zeolite molecular sieves, which are subjected to a combined modification with silver and lanthanum, were obtained by drying at 120° C. and calcining in the air at 550° C. for 6 hours after decanting the upper liquid layer.

4) Ag—La-HZSM-5 and Ag—La-HZSM-11 zeolite molecular sieves obtained in step 3) were each impregnated with tetraethyl orthosilicate (TEOS) at ambient temperature for 24 hours, and HZSM-5 and HZSM-11 molecular sieve catalysts modified with silver, lanthanum, and silane were obtained by drying at 120° C. and calcining in the air at 550° C. for 6 hours after decanting the upper liquid layer. The catalysts were named as MTPP-08 and MTPP-09, respectively. The loading amounts of respective elements in MTPP-08 and MTPP-09 catalysts were analyzed and measured by X-ray fluorescence diffraction (XRF). for the MTPP-08 catalyst, the loading amount of Ag was 1.02 wt %, the loading amount of La was 1.25 wt %, and the loading amount of silanized Si was 2.32 wt %; for the MTPP-09 catalyst, the loading amount of Ag was 1.13 wt %, the loading amount of La was 1.18 wt %, and the loading amount of silanized Si was 2.16 wt %.

Example 2

Preparation of p-Xylene and Propylene from Methanol

According to the reaction process flow shown in FIG. 2, the MTPP-08 catalyst prepared in Example 1 was charged into a first reaction zone and a second reaction zone of a fixed reactor respectively (10 g for each reaction zone). Aromatization reaction of methanol was mainly performed in the first reaction zone, and the product after reaction was passed into the second reaction zone, wherein the mass hourly space velocity of feeding methanol is 2 $h^{-1}$ and the reaction temperature is 500° C. Here, an ethylene-enriched $C_2^-$ component and methanol in the reaction product were passed together into the second reaction zone for reaction. Here, ethylene/methanol (molar ratio) was 1/1, the reaction temperature was 400° C., and alkylation reaction of ethylene and methanol was performed in the second reaction zone.

The composition of mixed products of the first reaction zone and the second reaction zone was analyzed online by using a gas chromatograph respectively. The product distribution was as shown in Table 1 after resultant water was removed, and the product distribution was as shown in Table 2 after the returned component of $C_2^-$ was further removed.

It can be seen from Table 2 that, after the $C_2^-$ component was removed from total products of the first reaction zone and the second reaction zone, in the products, the selectivity of propylene was 42.52 wt %, the selectivity of p-xylene was 38.05 wt %, and the overall selectivity of propylene and p-xylene was 80.57 wt %. The selectivity of p-xylene in xylene isomers was 98.98 wt %.

TABLE 1

| Catalyst | MTPP-08 |
|---|---|
| Feeding time (hour) | 1 |
| Selectivity of $C_2^-$ component (wt %) | 22.04 |
| Selectivity of p-xylene in xylene isomers (wt %) | 98.98 |
| Product distribution (wt %)* | |
| $CH_4$ | 3.04 |
| $C_2H_4$ | 18.30 |
| $C_2H_6$ | 0.70 |
| $C_3H_6$ | 33.15 |
| $C_3H_8$ | 1.50 |
| $C_4$ | 5.61 |
| $C_5$ | 1.84 |
| Benzene | 0.02 |
| Toluene | 0.16 |
| Ethylbenzene | 0.02 |
| p-Xylene | 29.66 |
| m-Xylene | 0.15 |
| o-Xylene | 0.15 |
| $\geq C_9$ | 5.70 |
| Total | 100.00 |

*wt %, weight percentage composition of products, the same shall apply hereinafter.

TABLE 2

| Catalyst | MTPP-08 |
|---|---|
| Feeding time (hour) | 1 |
| Selectivity of propylene + p-xylene (wt %) | 80.57 |
| Selectivity of p-xylene in xylene isomers (wt %) | 98.98 |
| Product distribution (wt %) | |
| $C_3H_6$ | 42.52 |
| $C_3H_8$ | 1.92 |
| $C_4$ | 7.19 |
| $C_5$ | 2.37 |
| Benzene | 0.02 |
| Toluene | 0.20 |
| Ethylbenzene | 0.02 |
| p-Xylene | 38.05 |
| m-Xylene | 0.19 |
| o-Xylene | 0.20 |
| $\geq C_9$ | 7.31 |
| Total | 100.00 |

Example 3

Preparation of p-Xylene and Propylene from Methanol

According to the reaction process flow shown in FIG. 3 or 4, the MTPP-08 catalyst and the MTPP-09 catalyst prepared in Example 1 were charged into a first reaction zone and a second reaction zone respectively (10 g for each reaction zone). Aromatization reaction of methanol was performed in the first reaction zone, wherein the mass hourly space velocity of feeding methanol is 2 $h^{-1}$ and the reaction temperature is 500° C. Alkylation reaction of ethylene and methanol was performed in the second reaction zone. An ethylene-enriched $C_2^-$ component and methanol in the methanol conversion reaction product distribution in Comparative Example were passed together into the second reaction zone for reaction, wherein ethylene/methanol (molar ratio) was 1/1, and the reaction temperature was 400° C.

The composition of mixed products of the first reaction zone and the second reaction zone was analyzed online by using a gas chromatograph respectively. The product distribution was as shown in Table 3 after resultant water was removed, and the product distribution was as shown in Table 4 after the $C_2^-$ component was further removed.

It can be seen from Table 4 that, after the $C_2^-$ component was removed from total products of the first reaction zone and the second reaction zone, in the products, the selectivity of propylene was 53.62 wt %, the selectivity of p-xylene was 30.59 wt %, and the overall selectivity of propylene and p-xylene was 84.21 wt %. The selectivity of p-xylene in xylene isomers was 99.32 wt %.

TABLE 3

| Catalyst | MTPP-08/09 |
|---|---|
| Feeding time (hour) | 1 |
| Selectivity of $C_2^-$ components (wt %) | 24.98 |
| Selectivity of p-xylene in xylene isomers (wt %) | 99.32 |
| Product distribution (wt %) | |
| $CH_4$ | 3.33 |
| $C_2H_4$ | 20.60 |
| $C_2H_6$ | 1.04 |
| $C_3H_6$ | 40.23 |
| $C_3H_8$ | 1.70 |
| $C_4$ | 4.24 |
| $C_5$ | 1.40 |
| Benzene | 0.01 |
| Toluene | 0.05 |
| Ethylbenzene | 0.01 |
| p-Xylene | 22.95 |
| m-Xylene | 0.05 |
| o-Xylene | 0.11 |
| $\geq C_9$ | 4.28 |
| Total | 100.00 |

TABLE 4

| Catalyst | MTPP-08/09 |
|---|---|
| Feeding time (hour) | 1 |
| Selectivity of propylene + p-xylene (wt %) | 84.21 |
| Selectivity of p-xylene in xylene isomers (wt %) | 99.32 |
| Product distribution (wt %) | |
| $C_3H_6$ | 53.62 |
| $C_3H_8$ | 2.27 |
| $C_4$ | 5.65 |
| $C_5$ | 1.86 |
| Benzene | 0.02 |
| Toluene | 0.06 |
| Ethylbenzene | 0.02 |
| p-Xylene | 30.59 |
| m-Xylene | 0.06 |
| o-Xylene | 0.15 |
| $\geq C_9$ | 5.70 |
| Total | 100.00 |

Comparative Example 1

Production of p-Xylene and Joint Production of Propylene from Methanol without Further Reaction by Returning $C_2^-$ Component 10 g of the MTPP-08 catalyst prepared in Example 1 was charged into a reactor for performing methanol conversion reaction, wherein the mass hourly space velocity of methanol was 2 $h^{-1}$ and the reaction temperature was 500° C. The composition of products was analyzed online by using a gas chromatograph. The product distribution was as shown in Table 5 after resultant water was removed.

When feeding only methanol for reaction were carried out in the reactor, the selectivity of propylene in the products was only 29.48 wt %.

TABLE 5

Results of methanol conversion reaction

| Catalyst | MTPP-08 |
|---|---|
| Feeding time (hour) | 1 |
| Conversion rate of methanol (%) | 95.68 |
| Selectivity of p-xylene in xylene isomers (wt %) | 99.42 |
| Product distribution (wt %)* | |
| $CH_4$ | 2.04 |
| $C_2H_4$ | 21.34 |
| $C_2H_6$ | 0.13 |
| $C_3H_6$ | 29.48 |
| $C_3H_8$ | 0.31 |
| $C_4$ | 6.29 |
| $C_5$ | 2.08 |
| Benzene | 0.02 |
| Toluene | 0.23 |
| Ethylbenzene | 0.02 |
| p-Xylene | 34.34 |
| m-Xylene | 0.04 |
| o-Xylene | 0.16 |
| $\geq C_9$ | 3.52 |
| Total | 100.00 |

This invention has been described in detail above, but this invention is not limited to specific embodiments described herein. It will be understood by the person skilled in the art that other modifications and variations can be made without departing from the scope of the invention. The scope of the invention is defined by the appended claims.

What is claimed is:

1. A method for preparing p-xylene and propylene from methanol and/or dimethyl ether in a reaction system comprising a first reaction zone and a second reaction zone, comprising the steps of:
   a) passing a first portion of a raw material containing methanol and/or dimethyl ether through the first reaction zone to be in contact with a catalyst I to obtain an intermediate product stream,
   b) passing the intermediate product stream and a second portion of the raw material containing methanol and/or dimethyl ether through the second reaction zone to be in contact with a catalyst II to obtain a final product stream comprising a $C_6^+$ component, a $C_4$-$C_5$ component, a $C_3$ component, an ethylene-enriched $C_2^-$ component, and $H_2O$;
   c) passing the final product stream to a separation system to recover the $C_6^+$ component, the $C_4$-$C_5$ component, the $C_3$ component, the ethylene-enriched $C_2^-$ component and $H_2O$, respectively, and returning the ethylene-enriched $C_2^-$ component to the second reaction zone;
   d) further separating the recovered $C_6^+$ component to obtain a product p-xylene; and
   e) further separating the recovered $C_3$ component to obtain propylene;
   wherein each of the catalyst I and the catalyst II independently comprises a modified zeolite molecular sieve catalyst obtained from ZSM-5 and/or ZSM-11 zeolite molecular sieve modified with a precious metal, a rare earth metal, and a siloxanyl compound.

2. The method according to claim 1, wherein the first reaction zone and the second reaction zone are in the same reactor.

3. A method for preparing p-xylene and propylene from methanol and/or dimethyl ether in a reaction system comprising a first reaction zone and a second reaction zone, comprising the steps of:
   a) passing a first portion of a raw material containing methanol and/or dimethyl ether through the first reaction zone to be in contact with a catalyst I for aromatization reaction to obtain a resultant A,
   b) passing the resultant A to a separation system, and recovering and returning an ethylene-enriched $C_2^-$ component to the second reaction zone,
   c) passing a second portion of the raw material containing methanol and/or dimethyl ether through the second reaction zone to be in contact with a catalyst II to obtain a resultant B;
   d) passing the resultant B to the separation system such that the resultant B is subjected to separation in the separation system along with the resultant A to recover a $C_6^+$ component, a $C_4$-$C_5$ component, a $C_3$ component, the ethylene-enriched $C_2^-$ component, and $H_2O$, respectively;
   e) further separating the recovered $C_6^+$ component to obtain a product p-xylene; and
   f) further separating the recovered $C_3$ component to obtain a product propylene;
   wherein each of the catalyst I and the catalyst II independently comprises a modified zeolite molecular sieve catalyst obtained from ZSM-5 and/or ZSM-11 zeolite molecular sieve modified with a precious metal, a rare earth metal, and a siloxanyl compound.

4. The method according to claims 1 or 3, wherein, the catalyst I and the catalyst II contain the same or different modified zeolite molecular sieve catalysts(s).

5. The method according to claim 1 or 3, wherein the siloxanyl compound used in the siloxanyl compound modification has a structural formula as shown below:

wherein $R_1$, $R_2$, $R_3$, and $R_4$ are each independently a $C_{1-10}$ alkyl group.

6. The method according to claim 1 or 3, wherein the reaction system comprises a plurality of reactors connected in series and/or in parallel.

7. The method according to claim 6, wherein the plurality of reactors are selected from a fixed bed reactor, a fluidized bed reactor, and a moving bed reactor.

8. The method according to claim 3, wherein the first reaction zone comprises a reactor or a plurality of reactors connected in series and/or in parallel; the second reaction zone comprises a reactor or a plurality of reactors connected in series and/or in parallel; and the first reaction zone and the second reaction zone are connected in parallel.

* * * * *